(12) United States Patent
Sansinena et al.

(10) Patent No.: US 7,442,403 B2
(45) Date of Patent: Oct. 28, 2008

(54) MEMBRANE ARCHITECTURES FOR ION-CHANNEL SWITCH-BASED ELECTROCHEMICAL BIOSENSORS

(75) Inventors: Jose-Maria Sansinena, Los Alamos, NM (US); Antonio Redondo, Los Alamos, NM (US); Basil I. Swanson, Los Alamos, NM (US); Chanel Kitmon Yee, Davis, CA (US); Annapoorna R. Sapuri/Butti, Davis, CA (US); Atul N. Parikh, Woodland, CA (US); Calvin Yang, Davis, CA (US)

(73) Assignee: Los Alamos National Security, LLC, Los Alamos, NM (US)

( * ) Notice: Subject to any disclaimer, the term of this patent is extended or adjusted under 35 U.S.C. 154(b) by 461 days.

(21) Appl. No.: 11/072,720

(22) Filed: Mar. 4, 2005

(65) Prior Publication Data
US 2005/0244487 A1 Nov. 3, 2005

Related U.S. Application Data

(60) Provisional application No. 60/550,672, filed on Mar. 5, 2004.

(51) Int. Cl.
*B05D 3/06* (2006.01)
*C12Q 1/70* (2006.01)

(52) U.S. Cl. .................. 427/2.13; 427/2.11; 216/66

(58) Field of Classification Search ............... 257/40; 435/6; 205/3, 7, 140, 205, 266; 422/68.1; 427/2.13, 2.11; 216/66
See application file for complete search history.

(56) References Cited

U.S. PATENT DOCUMENTS 7,132,122 B2 * 11/2006 Parikh et al. ............... 427/2.13

* cited by examiner

*Primary Examiner*—Maryam Monshipouri
(74) *Attorney, Agent, or Firm*—Bruce H. Cottrell; Juliet A. Jones

(57) ABSTRACT

The present invention is directed to a process of forming a bilayer lipid membrane structure by depositing an organic layer having a defined surface area onto an electrically conductive substrate, removing portions of said organic layer upon said electrically conductive substrate whereby selected portions of said organic layer are removed to form defined voids within said defined surface area of said organic layer and defined islands of organic layer upon said electrically conductive substrate, and, depositing a bilayer lipid membrane over the defined voids and defined islands of organic layer upon said substrate whereby aqueous reservoirs are formed between said electrically conductive substrate and said bilayer lipid membrane, said bilayer lipid membrane characterized as spanning across the defined voids between said defined islands. A lipid membrane structure is also described together with an array of such lipid membrane structure.

5 Claims, 5 Drawing Sheets

Fig. 4

A) No bounded receptors (closed)
B) Specific target-neurotoxin bounded to the receptor (open)

MEMBRANE ARCHITECTURES FOR ION-CHANNEL SWITCH-BASED ELECTROCHEMICAL BIOSENSORS

RELATED APPLICATIONS

This application claims the benefit of Provisional Application No. 60/550,672 filed on Mar. 5, 2004.

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates to lipid membrane architectures useful for ion-channel switch-based electrochemical biosensors, to a process of forming such lipid membrane architectures, and to an array structure useful for ion-channel switch-based electrochemical biosensors.

BACKGROUND OF THE INVENTION

Ion-channel based biological systems have not been extensively employed in current sensor technology because of the problems in reproducing a native-like microenvironment necessary for proper functioning. There are several problems to overcome in achieving this approach. First, a lipid bilayer must be formed upon a solid surface and the lipid bilayer should be sufficiently flexible and defect free such that ion-channel activity can actually be measured. Second, the lipid membrane must be in a physical state where biological molecules can function as if they are in a natural system. Third, an ionic medium needs to be entrapped between the membrane and the supporting electrode in order to facilitate the ion exchange through the ion-channels incorporated into the membrane.

A previous approach based on gramicidin-A pairs, by Cornell et al., Nature, vol. 387, pp. 580-583 (1997), has limitations related to a choice of ion-channel switching mechanism that is different from any of those present in cell membranes. Further, the preparation of the ionic reservoir structure between the membrane and the supporting electrode evidences high experimental difficulties. Their work has shown switched ion-channel sensors wherein the mode of transduction relies upon two antibodies for recognition, i.e., recognition opens or closes an ion channel by dragging gramacidin within the upper leaf away from gramacidin within the lower leaf that is anchored to the substrate surface thereby closing the channel. Another drawback to their approach is the need for a conjugation step (typically biotin-avidin) to attach the antibodies to molecules that anchor them to either the gramicidin or to a membrane spanning molecule that is also attached to the substrate surface.

Another previous approach has involved surface micro-patterning methods and this solid state approach has been useful for patterning supported phospholipid bilayer membranes. Such patterned phospholipid bilayer membranes have played an important role in the understanding, emulation, patterning and exploitation of selected functions of cell membranes for fundamental biophysical research and other biomedical and sensing technologies. Such micro-patterning of supported lipid membranes has been achieved by methods falling into two broad categories. The first is the use of pre-patterned substrate surfaces that present chemical and/or electrostatic barriers to membrane formation (see, e.g., Groves et al., Biophys. J., vol. 69, pp. 1972-1975 (1995)). The second is application of soft lithographic methods of patterned deposition, e.g., stamping, or removal, e.g., blotting, using polymeric stamps (see, e.g., Hovis et al., Langmuir, vol. 16, pp. 894-897 (2000).

Methods requiring substrate pre-patterning can depend upon the prior deposition of exogenous materials on the substrate surface and form single patterns. While methods based on polymer stamps can circumvent these issues, they require optimization of the physical contact, associated with contact pressure, and deformability of the polymer stamps. Moreover, some difficulties remain that are associated with achieving uniform contact for large-area patterning.

Morigaki et al. have recently described a photochemical method for micro-patterning of supported lipid membranes (see, Angew. Chemie. Int. Ed., vol. 40, pp. 172-174 (2001)). This method is based on a photolithographic polymerization of a diacetylene lipid that polymerizes with neighboring areas of lipids that are appropriately masked to avoid the polymerization process. The formation of a two-dimensional polymeric network makes the irradiated bilayer insoluble in organic solvents. By removing the monomeric lipids with an organic solvent, a two-dimensional corral structure is created for the incorporation of biologically relevant lipid bilayer membranes into the corrals. It was demonstrated that the newly incorporated bilayers retained their fluidity, whereas the polymerized lipid bilayer functioned as an effective barrier for the lateral diffusion of lipids. Despite these positive results in membrane micro-patterning, this method is limited by the need for photochemically polymerizable lipids.

Other approaches have relied upon single ion-channel proteins supported by a bilayer that spans a hole in a substrate such as a sheet of polytetrafluoroethylene (PTFE) or another hydrophobic polymer. Unfortunately, these approaches yield membranes with insufficient stability for most applications. Even small vibrations make them very unstable and easy to break. These black lipid membranes are particularly susceptible to disruption by vibrations or shock and typically can only be maintained for about 24 hours under the most favorable conditions. A similar approach has been described by Cheng et al., Langmuir, vol. 17, pp. 1240-1242 (2001), and involved a bilayer supported over a porous hydrophilic polymer.

Methods to create arrays of membranes would enable high-throughput screening of multiple targets against multiple drug-candidates. Arrays of membranes may be obtained by fabricating grids of titanium oxide on a glass substrate as titanium oxide resists the adsorption of lipids (Boxer, S. G. et al. Science 1997, 275, 651-653; and Boxer, S. G. et al. Langmuir 1998, 14, 3347-3350). Micro-pipeting techniques have been used to spatially address each corralled lipid-binding region (Cremer et al., J. Am. Chem. Soc., vol. 121, pp. 8130-8131 (1999)). However, these methods are cumbersome and require the fabrication of patterned surfaces. To make membrane arrays by printing membranes on unpatterned surfaces, it would be necessary to confine the membrane to the printed areas without lateral diffusion of the membrane molecules to the unprinted areas. Boxer et al. demonstrated that it was possible to pattern lipids on glass surfaces by microcontact printing using polydimethylsiloxane (PDMS) stamps "inked" with phosphatidylcholine. They attributed the lateral confinement of the lipids to the stamped regions, to the self-limiting expansion of phosphatidylcholine membranes to about 106% of the original printed areas (Hovis et al., Langmuir, vol. 16, pp. 894-897 (2000)). The methods used by Boxer et al., however, have certain limitations. First, Boxer et al. carried out the stamping of lipids on surfaces immersed under water. Second, lipids adsorbed on the bare-glass substrates used by Boxer et al. spontaneously desorbed when drawn through an air-water interface. In WO 01/20330, Cremer et al., propose the use of spatially addressed lipid bilayer arrays that remain submerged underwater to preserve the planar support structure. Such systems may not be practical for robust, high throughput, microarray based assays. Moreover, this approach could not be used to pattern addressable lipid bilayers onto conducting metal substrates.

Still other solutions to the existing problems have been sought.

The present inventors have now developed a simple light-directed method for patterning supported lipid membranes over large substrate areas in a non-contact manner and without the need for prior substrate patterning.

SUMMARY OF THE INVENTION

To achieve the foregoing and other objects, and in accordance with the purposes of the present invention, as embodied and broadly described herein, the present invention provides a process of forming a bilayer lipid membrane structure including depositing an organic layer having a defined surface area onto an electrically conductive substrate, removing portions of the organic layer upon the electrically conductive substrate whereby selected portions of the organic layer are removed to form defined voids within the defined surface area of the organic layer and defined islands of organic layer upon the electrically conductive substrate, and, depositing a bilayer lipid membrane over the defined voids and defined islands of organic layer upon the substrate whereby aqueous reservoirs are formed between the electrically conductive substrate and the bilayer lipid membrane, the bilayer lipid membrane characterized as spanning across the defined voids between the defined islands.

The present invention further provides a lipid membrane structure including an electrically conductive substrate, an organic layer upon the electrically conductive substrate, the organic layer having a defined pattern such that there are defined islands of the organic layer separated by defined voids, and a bilayer lipid membrane over the defined voids and defined islands of the organic layer upon the electrically conductive substrate whereby an aqueous reservoir is formed between the electrically conductive substrate and the bilayer lipid membrane.

In one embodiment of the invention, an array of such individual lipid membrane structures is provided.

BRIEF DESCRIPTION OF THE DRAWINGS

FIG. 4A-4B show a schematic illustration of a switching mechanism of a ligand-gated ion channel triggered by a specific binding event.

DETAILED DESCRIPTION

The present invention is concerned with membrane architectures and in particular an array structure for ion-channel switch-based electrochemical biosensors. The present invention is further concerned with a method for patterning supported phospholipids membranes over large substrate areas in a non-contact manner and without the need for any prior substrate patterning.

Figure 1:
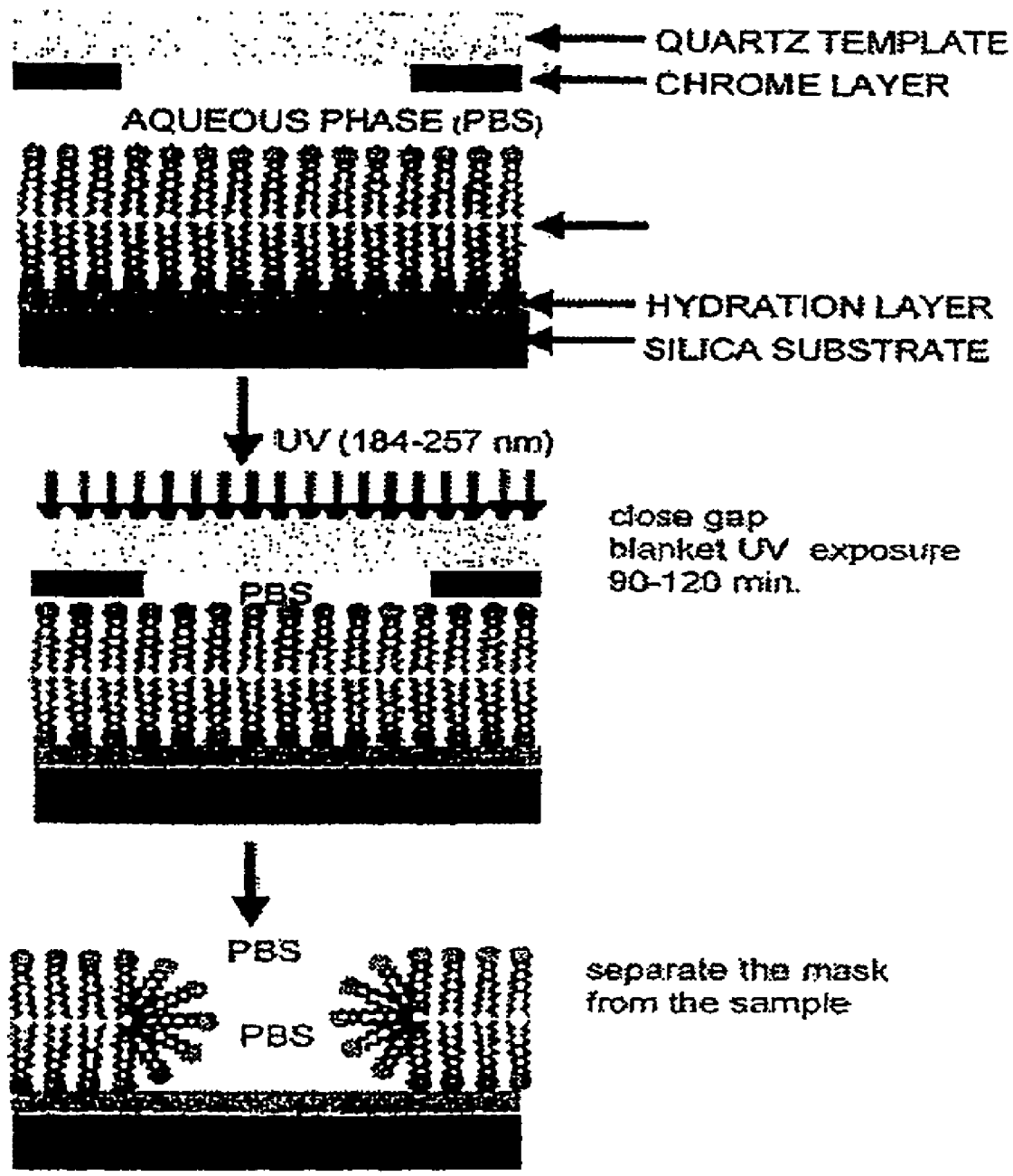
FIG. 1 shows a schematic illustration of the direct patterning of voids within lipid membrane bilayers using deep UV photolithography in accordance with the present invention.

In the present invention, the process of forming the desired membrane structure or architecture is shown in FIG. 1 and begins with the preparation of an organic layer upon an electrically conductive surface. The organic layer can be, e.g., a bilayer lipid membrane, a hybrid bilayer lipid membrane, or a self assembled multilayer. The self assembled multilayer can include multiple layers of one or more polyelectrolyes and can further include, in addition to the polyelectrolytes, one or more layers of a conductive polymer such as polyaniline and the like. The multilayer could also be formed from alternating layers of organics self-assembled from solution onto the substrate (e.g., alkanethiols on gold capped with a layer of polyethylene glycol (PEG)).

An organic layer of self-assembled polyelectrolyte multilayers in accordance with the present invention can be prepared by using a layer-by-layer coating process. Such a layer-by-layer coating is based on the sequential adsorption of oppositely charged materials. "Layer-by-layer coating", as used herein, refers to a layer-by-layer alternative, physical deposition of two oppositely charged polymeric materials (polyionic materials) or of a vesicle with surface charges and a polyionic material having charges opposite of the charges of the vesicles on an article. The layer-by-layer coating of an article is not covalently bound to the core material of the article. In a layer-by-layer coating, each layer of a polyionic material is non-covalently bound to another layer of a different polyionic material. Formation of a layer-by-layer coating on an article may be accomplished in a number of ways, for example, as described in U.S. Pat. No. 6,451,871, such description incorporated herein by reference in its entirety. One suitable coating process involves solely dip-coating and dip-rinsing steps. Another coating process involves solely spray-coating and spray-rinsing steps. However, a number of alternatives involve various combinations of spray- and dip-coating and rinsing steps would be recognized by those skilled in the art.

The term "polyelectrolyte" is meant to refer to polymers that have incorporated ionic or ionizable groups in the main chain or side chain. Such a "polyelectrolyte" can also be a copolymer of ionic/ionizable and nonionic monomer units. Polyelectrolytes can be present in anionic form, cationic form or neutral form, preferably in anionic form or cationic form. Examples of anionic polyelectrolytes include poly(styrenesulfonic acid), polyvinyl(sulfonate), poly(acrylic acid), dextran sulfate, poly(amidoamine) dendrimers (PAMAM), (carboxyl-terminated, half generation) and carboxycellulose. Examples of cationic polyelectrolytes include poly(allylamine hydrochloride), poly(vinylamine), poly(ethyleneimine), poly(diallylammonium chloride), PAMAM dendrimers (amino-terminated, full generation) and poly(2-vinylpyridine). Examples of ionic copolymers include poly (acrylic acid-co-acrylamide) and poly(diallylammonium chloride-co-acrylamide). Carboxyl, sulfate, sulfonate, phosphate and phosphonate groups are typical functional groups of anionic polyelectrolytes. Typical cationic functionalities include primary, secondary, tertiary and quaternary amine groups as well as $R_3S^+$ groups.

After deposition of an organic layer onto a substrate, portions of the organic layer can be removed. In one embodiment, such portions can be removed by a light-directed method of patterning supported phospholipids membranes. While such a light-directed approach is generally analogous to solid-state lithographic methods developed for dry-state DNA and peptide arrays, it can be applicable for the aqueous phase and fluid bilayer lipid membranes (BLM). The organic material of the first layer can be removed in accordance with the process described for the removal of organics by Clark et al., "A New Application of UV-Ozone Treatment in the Preparation of Substrate-Supported, Mesoporous Thin Films", Chem. Mater., 2000, 12, 3879-3884. The present invention can rely on spatially-directed illumination of phospholipids bilayers submerged in an aqueous environment ambient to UV light. The pattern of exposure to light through a mask, or by other spatially addressable means, can determine the relief pattern generated within the bilayer.

Suitable masking can be accomplished by use of a quartz/chrome photomask. Such a mask is previously formed with the desired configuration for void formation with the masked areas of the first bilayer lipid membrane remaining after exposure, e.g., to the UV light.

A lithographically produced quartz mask, e.g., an array of square opaque elements over an ultraviolet (UV) light transparent quartz mask, can then be positioned over the organic layer. UV light in the range of 184-257 nm, produced by a low pressure Hg discharge grid-lamp in a quartz envelope is used for the complete removal of the organic material in the unmasked regions. Generally, exposure times of between about 1 hour and 2 hours are sufficient. An important aspect of the present removal process is that it can be accomplished in an aqueous environment so that where the organic layer is a lipid membrane it can remain within such an aqueous environment during removal of selected portions. In the case where the organic layer is not a lipid membrane, then the present removal process can be conducted in air and may then be stored in air prior to deposition of a subsequent spanning bilayer lipid membrane.

Upon separation of the mask from the sample, highly controlled patterns of the organic layer, e.g., a bilayer membrane, with intact lipid patches (i.e., hybrid bilayer membrane islands isolated from one another by the voids generated through removal of selected portions of the organic layer) in areas masked from UV exposure and void areas free of organic material around such islands can be formed.

The removal of portions of the initial organic layer, e.g., the first hybrid bilayer membrane, generates defined voids within the surface area of the organic layer while leaving islands of the organic layer separated by such voids. Because there is no further supply of organic material, these islands can remain as intact islands and not migrate together. These voids provide a subsequent opportunity to form reservoirs, e.g., aqueous reservoirs, within a membrane structure.

The dimensions of such voids can generally be from as small as about 200 nm up to about 50 microns in size, preferably from about 500 nm to about 25 microns.

The height (i.e., the distance from the substrate surface to the spanning biayer lipid membrane) of the ionic reservoirs in the structures of the present invention can be varied by controlling the height of the organic layer, e.g., the first hybrid bilayer membrane. Further, the height of the aqueous reservoir could be increased by forming a double bilayer membrane as the first bilayer lipid membrane. In this manner, space may be provided for larger amounts of ionic fluid with the aqueous reservoir should that be desirable. Other manners of controlling the height of the aqueous reservoir may include using additional self assembled multilayers or may use a spacer material such as a polyethylene glycol (PEG) spacer material in conjunction with the organic layer.

In the present invention, the architecture of any first fluid membrane (as the organic layer) can include a regular bilayer membrane where both layers are deposited upon a suitable support surface, can include a hybrid bilayer, e.g., where a first layer is covalently attached to an oxide surface, or can include a bilayer cushioned by a polymer film. Suitable supported membranes useful in the practice of the present invention are generally described by Sackmann, in "Supported Membranes: Scientific and Practical Applications", Science, vol. 271, no. 5245, pp. 43-45, Jan. 5, 1996. Hybrid bilayer membranes may be more preferred as such membranes may have greater stability over time and may provide greater shelf lifetimes for some applications such as sensors.

Bilayer membranes can be formed upon a planar substrate, e.g., by initially forming vesicles followed by vesicle fusion or spreading of, e.g., phospholipid, bilayers onto a substrate as is well known to those skilled in the art.

The electrically conductive substrates can generally be a metal or can be an indium-tin oxide (ITO) substrate. The substrate may take a variety of configurations ranging from simple to complex, depending on the intended use of the array. Thus, the substrate could have an overall slide or plate configuration, such as a rectangular or disc configuration. Preferably, the substrate is planar.

When the substrate is a metal, a first layer (self-assembled) of an alkane thiol (thioalkane) can be initially reacted with the metal to provide a hydrophobic surface. Preferably, the thiol can be a thioalkyl compound and is selected from the group of a thioalkyl acid, thioalkyl alcohol, thioalkyl amine, and a halogen containing thioalkyl compound. Most preferably, the thioalkyl compound can be e.g., octadecathiol, or 16-mercaptohexadecanoic acid. Such compounds can be readily synthesized and/or purchased from commercial sources.

On a substrate such as ITO, a layer of a silane, e.g., an aminosilane such as 3-aminopropyltriethoxysilane, 3-aminopropyldiisopropylethoxysilane, 3-aminopropylmethyldiethoxysilane, 3-aminopropylpolydimethylsiloxane, N-(2-aminoethyl)-3-aminopropyltrimethoxysilane, and 3-aminopropyltris (methoxyethoxyethoxy)silane can be used as a linking agent between the ITO surface and subsequent materials by formation of a siloxane.

Figure 2:
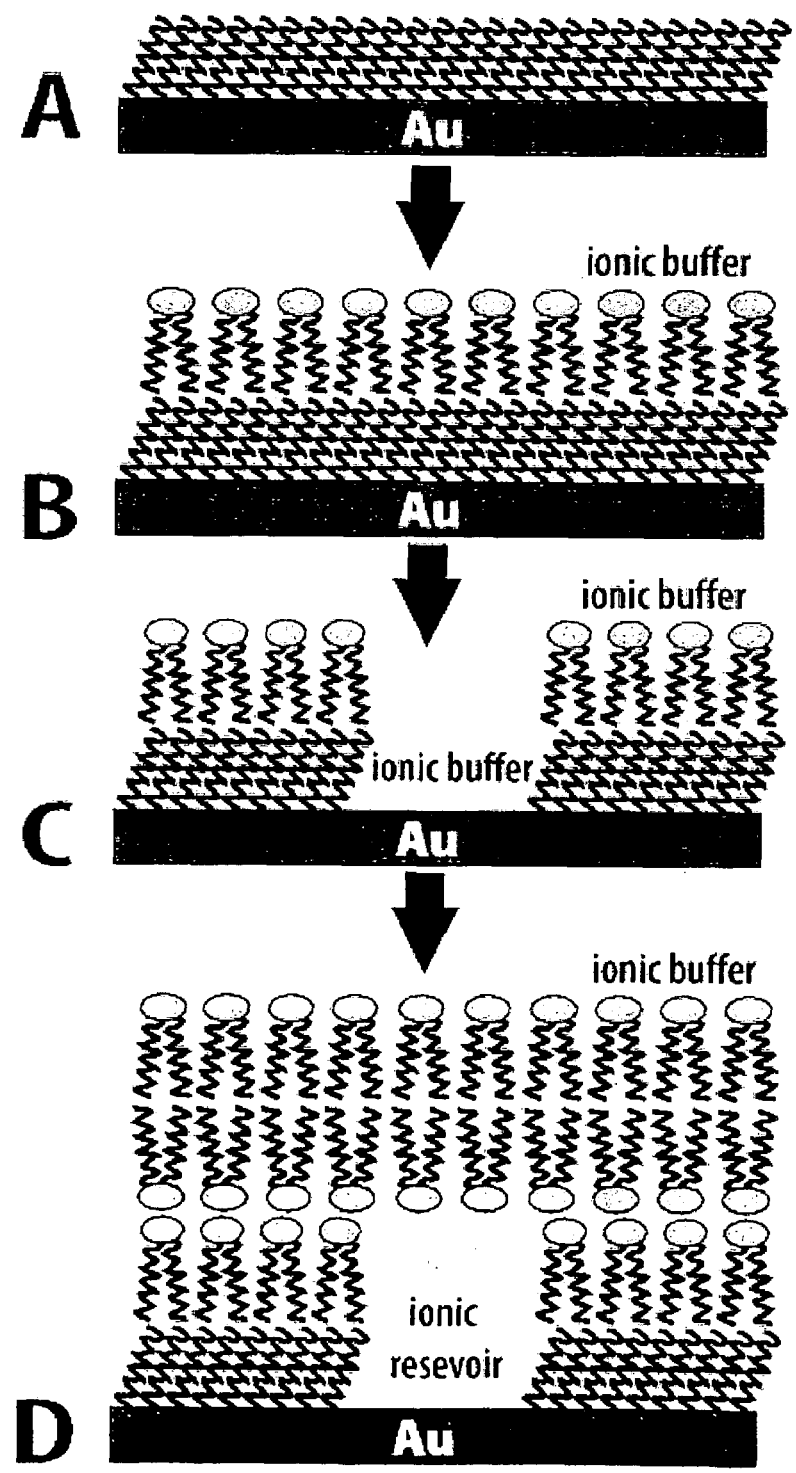
FIG. 2 shows a schematic illustration of an aqueous reservoir within a double lipid membrane bilayer.
Figure 3:
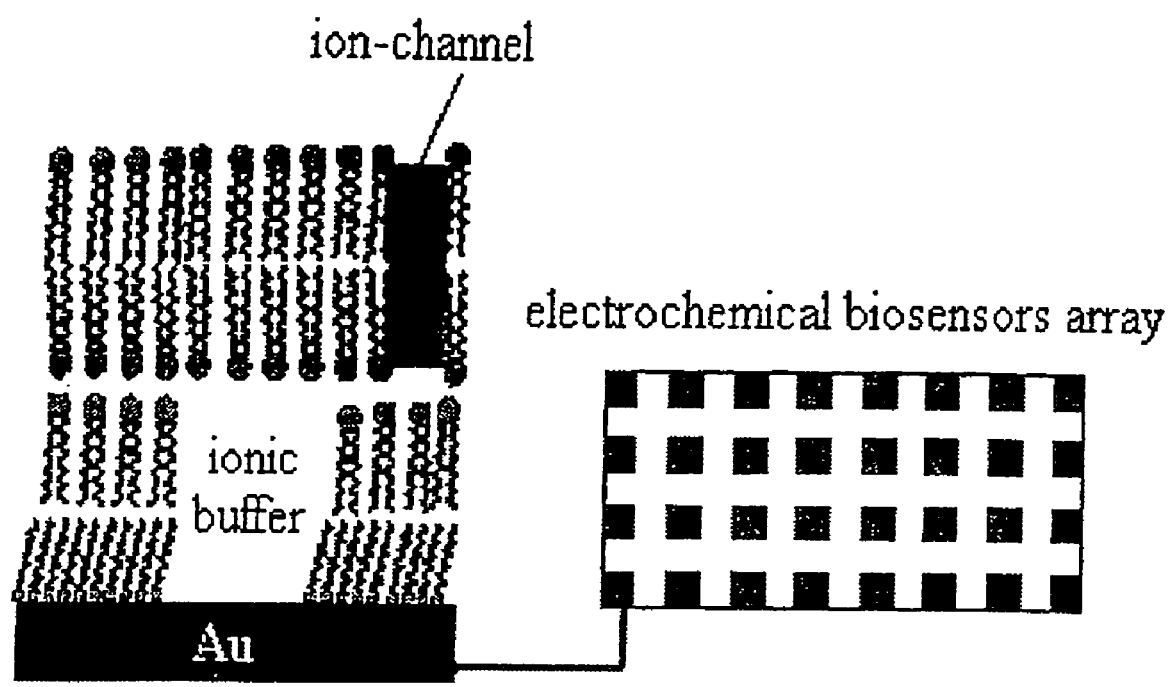
FIG. 3 shows a schematic illustration of an electrochemical biosensor array with ion channels incorporated into the secondary lipid bilayer that covers the ionic reservoirs connected to individual elecrodes.

Subsequent deposition of a bilayer lipid membrane that spans across the voids in the patterned, e.g., micro-patterned, organic layer yields aqueous reservoirs within a bilayer lipid membrane structure as shown in FIG. 2. In step A, alkanethiol (RSH) molecules are shown self-assembled upon the gold substrate. Then, in step B, vesicle spreading upon a hydrophobized RSH/Au substrate can yield a primary hybrid bilayer. Following photochemical patterning of the primary hybrid bilayer at step C, deposition of a secondary bilayer can span the void in the primary bilayer yielding the ionic reservoir. Where the organic layer is a first lipid bilayer, the result of the spanning bilayer lipid membrane is a double bilayer lipid membrane. In order to span across the voids, the bilayer membrane is formed from vesicles having sufficient size to span across the dimensions of the void while forming on top of the islands of the organic layer, e.g., a first bilayer lipid membrane separated by such voids. DMPC or POPC (1-palmitoyl-2-oleoyl-sn-glycero-3-phosphocholine) The lipids, i.e., phospholipids, can be natural or synthetic, but are conveniently selected from the phosphatidylcholine type derived from the natural lipids and mixtures thereof. These compounds are 1,2-dipalmitoyl, 1,2-dimyristoyl and 1-palmitoyl-2-oleyl-sn-glycero-3-phosphocholines, in the laevorotatory (L-) configuration, normally abbreviated to DPPC, DMPC, and POPC.

Suitable vesicles include those generally referred to as giant unilamellar vesicles (GUV). Examples of GUV materials include 1,2-dimyristoyl-sn-glycero-3-phosphocholine (DMPC) and palmitoyl-oleoyl-phosphatidyl-choline (POPC) and dioleoyl-phosphatidyl-methylester (DOPME). Other suitable vesicles for the spanning layer in the present invention are well known to those skilled in the art.

Independent electrodes can then be connected to individual aqueous or ionic reservoirs. Conductance measurements across the membranes may then be carried out as is well understood by those skilled in the art.

Figure 5:
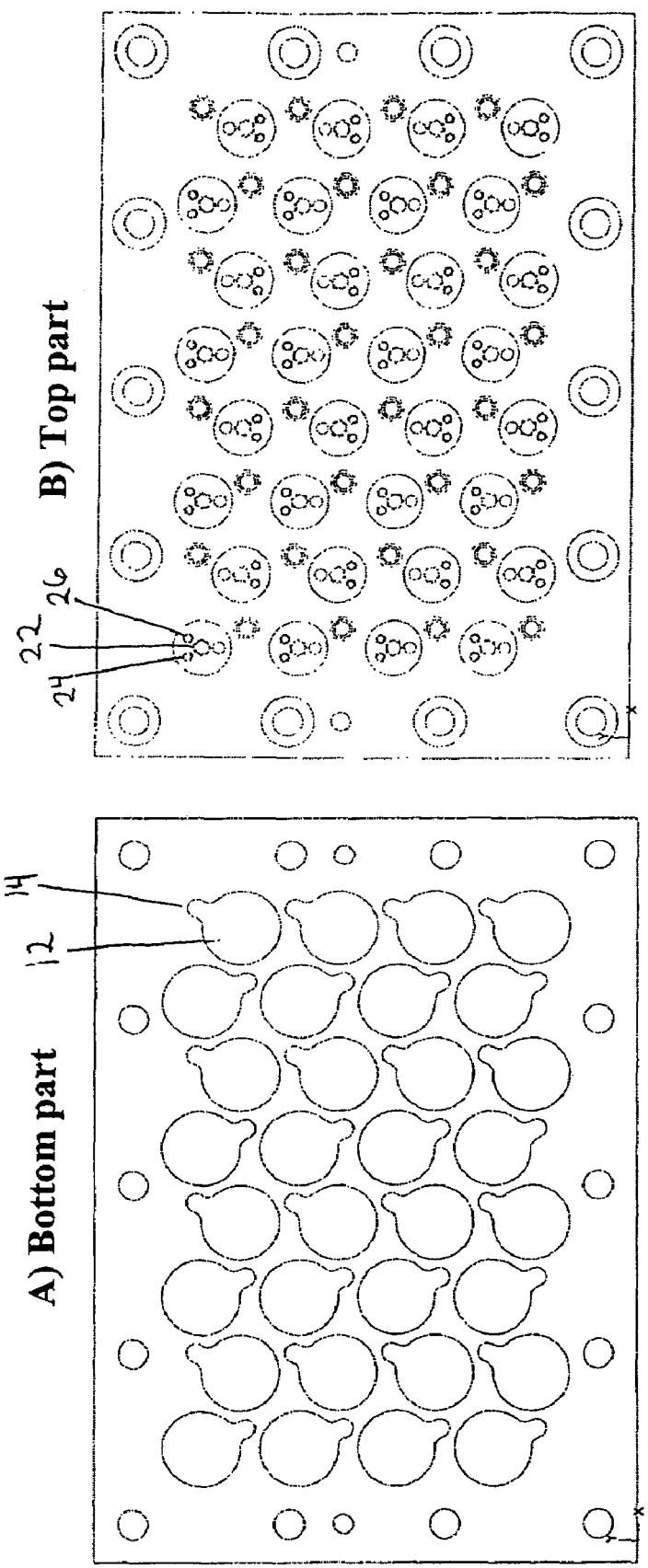
FIG. 5A-5B show a top view of an array of substrates for a lipid membrane array structure.

FIG. 5 shows a top view of the bottom and top parts of a sandwich-configured platform for a portable array useful for ion channel based electrochemical biosensors. In the bottom part, gold pads 12 have each been configured with a tab portion 14 for eventual electrical connection after a patterned lipid membrane structure is deposited thereon. In the top part, electrical connection is made down through central hole 22 while fluid inflow and outflow can be provided to the membrane structure though inlets 24 and 26. The top and bottom parts can be pressed together and fluid contained within the individual compartments by appropriate use of O-rings.

The present invention is more particularly described in the following examples, which are intended as illustrative only, since numerous modifications and variations will be apparent to those skilled in the art.

EXAMPLE 1

A first continuous supported bilayer lipid membrane (sBLM) was prepared by vesicle fusion upon a hydrophilic silica surface (electrically conductive gold surface pretreated by self-assembly of alkanethiol molecules of octadecathiol). To enable fluorescence measurements, vesicles were doped with appropriate concentrations of labeled lipids (e.g., 1 mole percent of 1,2-dihexadecanoyl-sn-glycero-3-phosphoethanolamine, triethylammonium salt (Texas Red-DHPE)).

Next, a lithographically produced quartz mask (e.g., an array of square opaque elements, such as chrome, over a UV transparent quartz mask) was then brought in contact with the sBLM. UV light in the 184-257 nm range, produced by either a low or medium pressure Hg lamp housed in a used quartz envelope. (10-20 mW/cm$^2$), was then directed through the mask at the sBLM samples submerged in phosphate buffered saline (PBS) solution for about 2 hours. Upon separation of the mask from the sBLM samples under the buffer solution, high fidelity patterns remained within the sBLM, the patterns including intact lipid patches in areas masked or shielded from the UV light and lipid-free regions in the UV-exposed areas. By this process, patterns of both voids and isolated membrane islands were created.

EXAMPLE 2

Formation of a supported lipid membrane including a double bilayer lipid membrane and ionic reservoirs was as follows. First, a patterned supported bilayer lipid membrane (sBLM) was prepared in accordance with Example 1. Then, a second continuous supported bilayer lipid membrane (sBLM) was prepared by vesicle fusion of giant unilamellar vesicles (1,2-dimyristoyl-sn-glycero-3-phosphocholine including 5 percent labeling of nitrobenzoxadiazole (NB-DPE) (a green dye) to allow monitoring of the deposited sBLM over the patterned supported bilayer lipid membrane. The giant unilamellar vesicles had a sufficient size to span across the patterned microvoids and formed continuous portions of a second sBLM spanning across voids in the underlying sBLM. Examination of the deposited second continuous supported bilayer lipid membrane by use of a green filter suggested that the membrane spanned the voids of the initial layer.

Preparation of GUV's and sizes: 2 mg of lipid solution in chloroform of lipids (8 percent of DOEPC (positively charged lipids), 3 percent of NBDPE, and 89 percent of DMPC) with mole percent. Then dried the chloroform with nitrogen blowing and in vacuum for 45 minutes. To the dried lipid film was added 0.5M sucrose at 45° C. and the mixture was kept at 37° C. overnight without disturbing. The next day GUV's had been formed. The size of the resultant GUV's by this procedure was about 10-25 um. The procedure to spread them was to add them on to patterned surfaces in small quantities.

The patterned bilayer of the fluorescent images was about 1 percent (1 percent Texas red DHPE and 99 percent DLPC) charged and the second bilayer was 5 percent charged (8 percent DOEPC (positively charged lipids), 3 percent NBDPE, and 89 percent DMPC). More equal positive charges may be tried in the future, e.g., 5 percent with same lipids as above to have more electrostatic repulsions. It is expected that results should be a more visible second bilayer and a more stable double bilayer structure.

Although the present invention has been described with reference to specific details, it is not intended that such details should be regarded as limitations upon the scope of the invention, except as and to the extent that they are included in the accompanying claims.

What is claimed is:

1. A lipid membrane structure comprising:
an electrically conductive substrate wherein said substrate further includes a layer of a thioalkane thereon;
an organic layer upon said electrically conductive substrate, said organic layer having a defined pattern such that there are defined islands of said organic layer separated by defined voids; and,
a bilayer lipid membrane over said defined voids and defined islands of said organic layer upon said electrically conductive substrate whereby an aqueous reservoir is formed between said electrically conductive substrate and said bilayer lipid membrane.

2. The lipid membrane structure of claim 1, wherein the organic layer is selected from the group consisting of a bilayer lipid membrane, a hybrid bilayer lipid membrane, and a self assembled multilayer.

3. The lipid membrane structure of claim 1 wherein each of said defined islands is separated by said defined voids from other adjacent defined islands at a distance of from about 200 nm to about 25 microns.

4. The lipid membrane structure of claim 1 wherein said organic layer includes multiple bilayer lipid membranes thereby increasing the height of said ionic reservoir within said structure.

5. The lipid membrane structure of claim 1 wherein said organic layer includes a self assembled multilayer of polyelectrolyes.

* * * * *